United States Patent [19]
Erdös et al.

[11] Patent Number: 5,240,662
[45] Date of Patent: Aug. 31, 1993

[54] PROCESS FOR THE PREPARATION OF SOLID PHARMACEUTICAL COMPOSITIONS

[75] Inventors: Sándor Erdös; Dénes Bezzegh; János Egri; Erzsébet Bárczay; Olga Magyar; Sümeg Katalin, all of Budapest, Hungary

[73] Assignee: EGIS Gyogyszergyar, Budapest, Hungary

[21] Appl. No.: 827,397

[22] Filed: Jan. 29, 1992

[30] Foreign Application Priority Data

Jan. 30, 1991 [HU] Hungary .................. 318/91

[51] Int. Cl.⁵ .............................. B29C 43/02
[52] U.S. Cl. ..................... 264/112; 264/109; 264/117; 424/470; 424/474
[58] Field of Search ......... 264/109, 117, 112; 424/468, 469, 470, 474

[56] References Cited

U.S. PATENT DOCUMENTS

| | | | |
|---|---|---|---|
| 3,632,778 | 1/1972 | Sheth et al. | 264/117 |
| 4,762,658 | 8/1988 | Rothfuss et al. | 264/122 |
| 4,832,957 | 5/1989 | Dempski et al. | 424/469 |

Primary Examiner—Mary Lynn Theisen
Attorney, Agent, or Firm—Beveridge, DeGrandi, Weilacher & Young

[57] ABSTRACT

The invention relates to a process for the preparation of solid pharmaceutical compositions. More specifically, the invention relates to a process for the preparation of tablets ensuring an increased active ingredient release, where said tablets comprise as active ingredient a mixture of L-3,4-dihydroxyphenylalanine and L-alpha-hydrazino-alpha-methyl-3,4-dihydroxyphenyl propionic acid in a (3–12):1 mass to mass ratio, which comprises admixing any of L-3,4-dihydroxyphenylalanine and L-alpha-hydrazino-alpha-methyl-3,4-dihydroxyphenyl propionic acid, or both of them, with a hydrophilic diluent, preferably lactose and/or microcrystalline cellulose, and optionally with a colouring agent, blending the mixture thus obtained with auxiliary agents conventionally used for the preparation of tablets and optionally with the other active ingredient, furthermore with a solution of stearin in an appropriate solvent, preferably an alkanol comprising 2 to 4 carbon atoms, drying and granulating the mixture thus obtained, optionally admixing further auxiliary agent(s) to the dry granulate, compressing it into tablets comprising 50 to 70% by mass of active ingredient and, if desired, applying a film-coating onto the surface of the tablets thus obtained. The process according to the invention provides tablets of appropriate quality with rapid active ingredient release.

7 Claims, No Drawings

PROCESS FOR THE PREPARATION OF SOLID PHARMACEUTICAL COMPOSITIONS

This invention relates to a process for the preparation of solid pharmaceutical compositions. More specifically, this invention relates to a process for the preparation of tablets or film-coated tablets with increased active ingredient release, where said tablets comprise as active ingredient a mixture of L-3,4-dihydroxyphenylalanine and L-alpha-hydrazino-alpha-methyl-3,4-dihydroxyphenyl propionic acid in a (3–12):1 mass to mass ratio.

It is known in the art that L-3,4-dihydroxyphenylalanine (levodopa), when used in combination with L-alpha-hydrazino-alpha-methyl-3,4-dihydroxyphenyl propionic acid (carbidopa), is useful in the treatment of Parkinson's disease (U.S. Pat. No. 3,769,424). Although in this specification there is a reference to the preparation of pharmaceutical compositions comprising as active ingredient a mixture of levodopa and carbidopa in a (0.2–8):1 mass to mass ratio, neither the composition itself nor the process for the preparation thereof are disclosed.

According to the requirements raised against tablets with increased active ingredient release comprising as active ingredient levodopa in combination with carbidopa, which are specified by US Pharmacopoeia XXII (page 226) being in force as from Jan. 1, 1990, at least 80% of the active ingredient content of the tablet should be released in a 0.1 n hydrogen chloride solution within 30 minutes, under definite circumstances. The composition of the tablets complying with these requirements and the process for the preparation thereof, however, are not provided for in said pharmacopoeia.

The aim of the invention was to elaborate a process for the preparation of tablets ensuring an increased release of the active ingredients, wherein 80% of the active ingredient content of the tablets are released, under the circumstances specified by US Pharmacopoeia XXII (page 226), within 5–10 minutes in a 0.1 n hydrogen chloride solution, furthermore the tablets meet the usual requirements of quality, that is, they are perfect and undamaged in appearance, properly solid etc.

According to the invention there is provided a process for the preparation of tablets or film-coated tablets with increased active ingredient release, where the tablets comprise as active ingredient a mixture of L-3,4-dihydroxyphenylalanine and L-alpha-hydrazino-alpha-methyl-3,4-dihydroxyphenyl propionic acid in a (3–12):1 mass to mass ratio. This process is characterized by admixing any of L-3,4-dihydroxyphenylalanine and L-alpha-hydrazino-alpha-methyl-3,4-dihydroxyphenyl propionic acid, or both of them, with a hydrophilic diluent, preferably lactose and/or microcrystalline cellulose, and optionally with a colouring agent, blending the mixture thus obtained with auxiliary agents conventionally used for the preparation of tablets and optionally with the other active ingredient, furthermore with a solution of stearin in an appropriate solvent, preferably an alkanol comprising 2 to 4 carbon atoms, drying and granulating the mixture thus obtained, optionally admixing further auxiliary agent(s) to the dry granulate, compressing it into tablets comprising 50 to 70% by mass of active ingredient and, if desired, applying a film-coating onto the surface of the tablets thus obtained.

Carbidopa is preferably used in the form of its monohydrate. The term "L-alpha-hydrazino-alpha-methyl-3,4-dihydroxyphenyl propionic acid" encompasses both the anhydrous carbidopa and its monohydrate.

In the process according to the invention the rapid release of the active ingredients is ensured by admixing any of the active ingredients, or both of them, with a hydrophilic diluent, preferably with lactose and/or microcrystalline cellulose, by exerting a shear force, that is, by passing the mixture through e.g. a hammer mill or a cogged plate grinder, or by using blade mixers of high-speed kneading machines.

The suitable appearance and mechanical stability of the tablets according to the invention is ensured by carrying out the aggregation with stearin dissolved in an organic solvent, wherein the stearing is used generally in an amount of 1.5 to 2.5% by mass related to the mass of the ready-made tablet As organic solvent preferably ethanol or isopropanol is used. The organic solution of stearin may contain a binder, such as methylmethacrylic acid ester polymer, too. This step attributes to the rapid release of the active ingredients.

The above specified effects of the application of stearin could not be aforeseen, as according to our experiences directed to the preparation of tablets with increased active ingredient release comprising as active ingredient a mixture of levodopa and carbidopa in a (3–12):1 mass to mass ratio without applying stearin dissolved in an organic solvent for the aggregation, the tablets adhere to the punch faces during compression. So in this way neither tablets of appropriate appearance can be obtained nor the release of the active ingredients achieves the desired rate.

Stearin is used as lubricant for the preparation of tablets [J. Am. Pharm. Ass., 45 (1), 51 (1956); 49 (1), 35 (1960)] in an amount of about 1% by mass, preferably in an amount not exceeding 1% by mass. According to practical experiences the mere presence of stearin may lead to the sticking of tablets, that is why it is surprising that by the application thereof this phenomenon can be eliminated. Besides, as stearin is insoluble in water, it could have been expected that in the presence thereof the release of the active ingredient would be retarded.

According to the invention stearin is used in an amount of at least 1.5% related to the mass of the ready-made tablet.

After the treatment with a hydrophilic diluent, such as lactose and/or microcrystalline cellulose, as conventional pharmaceutical auxiliary agent e.g. a further diluent; cellulose; a disintegrating agent, preferably carboxymethylcellulose or a low-substituted hydroxypropylcellulose; and a binder, preferably methylmethacrylic acid ester polymer, is used.

It is considered preferable to apply a low-substituted hydroxypropylcellulose, which may act both as a binder and as disintegrant.

If both of the active ingredients are treated with hydrophilic solvent(s), only the above specified auxiliary agents conventionally used for the preparation of tablets and the stearin solution are added to them. If only one of the active ingredients, generally carbidopa, is treated with hydrophilic diluent(s), the other ingredient, furthermore the auxiliary agents and the stearin solution are introduced to the mixture thus obtained.

After granulation as further auxiliary agents conventionally used for the preparation of tablets e.g. disintegrants, preferably carboxymethylcellulose; antiadhesives, preferably talc; glidants, preferably colloidal silicon dioxide; or lubricants, preferably magnesium stearate, can be used.

The tablets obtained during the tableting procedure can be film-coated, if desired, by methods known per se.

When tablets coloured in their material are to be produced, it is preferable to blend the colouring agent with the active ingredient(s) and with the hydrophilic diluent(s) by exerting a shear force. One may also proceed by colouring first the hydrophilic diluent(s) with the aqueous solution of a colouring agent, then after drying blending the mixture thus obtained with the active ingredient(s) by exerting a shear force. In both cases the procedure is continued by adding further auxiliary agents to the mixture and kneading it with the stearin solution.

Colouring may also be ensured by film-coating.

The process according to the invention provides tablets with rapid active ingredient release. The appropriate quality of the tablets is ensured without an unjustified increase of the amount of the auxiliary agents, so the active ingredient content of the tablets according to the invention may be as high as 70%.

The invention is illustrated in detail by the following non-limiting Examples.

EXAMPLE 1

A mixture of 1720 g of lactose and 1720 g of porous microcrystalline cellulose is thoroughly moistened with an aqueous solution of 2 g of indigo carmine, then dried. The coloured mixture thus obtained is admixed with 10 kg of levodopa and 1080 g of carbidopa monohydrate, then passed through a cogged plate grinder of Alpin type. 800 g of methylmethacrylic acid ester polymer (Eudragit L 100) and 160 g of cross-linked carboxymethylcellulose are added to the crushed product thus obtained and it is kneaded in a kneading machine with a solution of 280 g of stearin in 2200 g of ethanol. Then it is dried and regranulated. 400 g of talc, 80 g of magnesium stearate, 20 g of colloidal silicon dioxide (Aerosil, produced by Degussa) and 140 g of cross-linked carboxymethylcellulose are admixed to the dry granulate and the mixture is compressed into tablets of 10 mm diameter. Thus, tablets weighing 0.41005 g and having the following composition are obtained:

| | |
|---|---|
| levodopa | 0.250 g |
| carbidopa monohydrate | 0.027 g |
| lactose | 0.043 g |
| microcrystalline cellulose | 0.043 g |
| colouring agent (indigo carmine) | 0.00005 g |
| methylmethacrylic acid ester polymer | 0.020 g |
| cross-linked carboxymethylcellulose | 0.0075 g |
| stearin | 0.007 g |
| talc | 0.010 g |
| magnesium stearate | 0.002 g |
| colloidal silicon dioxide | 0.0005 g |
| | 0.41005 g |

The active ingredient release of the tablets thus obtained was examined by the method specified in US Pharmacopoeia XXII (page 226). 85% by mass of the active ingredients were released within 5 minutes.

EXAMPLE 2

A mixture of 1204 g of lactose and 3393.6 g of microcrystalline cellulose is thoroughly moistened with an aqueous solution of 8.4 g of indigo carmine and dried. The coloured mixture thus obtained is admixed with 7 kg of levodopa and 756 g of carbidopa monohydrate, then passed through a cogged plate grinder of Alpin type. To the crushed mixture 560 g of methylmethacrylic acid ester polymer (Eudragit L 100) and 434 g of low-substituted hydroxypropylcellulose are added, the mixture thus obtained is kneaded in a kneading machine with a solution of 224 g of stearin in 2200 g of ethanol, dried and granulated. To the dry granulate 336 g of talc, 70 g of magnesium stearate and 14 g of colloidal silicon dioxide are added and the mixture is compressed into tablets of 8 mm diameter. Thus, tablets weighing 0.2 g and having the following composition are obtained:

| | |
|---|---|
| levodopa | 0.1000 g |
| carbidopa monohydrate | 0.0108 g |
| lactose | 0.0172 g |
| microcrystalline cellulose | 0.04848 g |
| colouring agent (indigo carmine) | 0.00012 g |
| methylmethacrylic acid ester polymer | 0.0080 g |
| low-substituted hydroxypropylcellulose | 0.0002 g |
| stearin | 0.0032 g |
| talc | 0.0048 g |
| magnesium stearate | 0.0010 g |
| colloidal silicon dioxide | 0.0002 g |
| | 0.2000 g |

The active ingredient release of the tablets thus obtained was examined by the method specified in US Pharmacopoeia XXII (page 226). 83% by mass of the active ingredient were released within 5 minutes.

EXAMPLE 3

Tablets having the following composition are prepared by the method specified in Example 2:

| | |
|---|---|
| levodopa | 0.1000 g |
| carbidopa monohydrate | 0.0270 g |
| lactose | 0.0200 g |
| microcrystalline cellulose | 0.0520 g |
| colouring agent (quinoline yellow) | 0.0008 g |
| methylmethacrylic acid ester polymer | 0.0100 g |
| low-substituted hydroxypropylcellulose | 0.0060 g |
| stearin | 0.0040 g |
| talc | 0.0040 g |
| magnesium stearate | 0.0010 g |
| colloidal silicon dioxide | 0.0002 g |
| | 0.2300 g |

EXAMPLE 4

A mixture of 108 g of carbidopa monohydrate and 172 g of lactose is passed through a cogged plate grinder of Alpin type, then it is blended with 1000 g of levodopa, 166 g of microcrystalline cellulose, 48 g methylmethacrylic acid ester polymer (Eudragit L 100) and 16 g of cross-linked carboxymethylcellulose in a kneading machine. The mixture is moistened with a solution of 28 g of stearin in 220 g of ethanol, kneaded thoroughly, dried and regranulated. To the dry granulate 52 g of cross-linked carboxymethylcellulose, 40 g of talc, 8 g of colloidal silicon dioxide (Aerosil, produced by Degussa) and 8 g of magnesium stearate are added and the mixture is compressed into tablets of 10 mm diameter. Thus, tablets weighing 0.410 g are obtained with the following composition:

| | |
|---|---|
| levodopa | 0.250 g |
| carbidopa monohydrate | 0.0270 g |
| lactose | 0.043 g |
| microcrystalline cellulose | 0.040 g |
| methylmethacrylic acid ester polymer | 0.012 g |
| cross-linked carboxymethylcellulose | 0.017 g |
| stearin | 0.007 g |
| talc | 0.010 g |
| colloidal silicon dioxide | 0.002 g |
| magnesium stearate | 0.002 g |
| | 0.410 g |

The active ingredient release of the tablets thus obtained was examined by the method specified in US Pharmacopoeia XXII (page 226). 80% by mass of the active ingredient were released within 5 minutes.

EXAMPLE 5

One proceeds according to Example 4 except that 24 g of methylmethacrylic acid polymer (Eudragit L 100) are used, 28 g of stearin are dissolved in 192 g of a 12.5% by mass solution of methylmethacrylic acid polymer in isopropanol (Eudragit L 12.5 P) and moistening is carried out with the solution obtained.

EXAMPLE 6

A mixture of 400 g of levodopa, 108 g of carbidopa monohydrate and 104 g of lactose is blended in a hammer mill. Then it is kneaded in a kneading machine with 96 g of microcrystalline cellulose, 32 g of methylmethacrylic acid ester polymer (Eudragit L 100), 4 g of cross-linked carboxymethylcellulose and a solution of 16 g of stearin in 125 g of ethanol, dried and granulated. To the dry granulate 48 g of cross-linked carboxymethylcellulose, 24 g of talc, 4 g of colloidal silicon dioxide and 4 g of magnesium stearate are admixed and the mixture is compressed into tablets having 8 mm diameter. Thus, tablets weighing 0.21 g are obtained with the following composition:

| | |
|---|---|
| levodopa | 0.100 g |
| carbidopa monohydrate | 0.027 g |
| lactose | 0.026 g |
| microcrystalline cellulose | 0.024 g |
| methylmethacrylic acid ester polymer | 0.008 g |
| cross-linked carboxymethylcellulose | 0.013 g |
| stearin | 0.004 g |
| talc | 0.006 g |
| colloidal silicon dioxide | 0.001 g |
| magnesium stearate | 0.001 g |
| | 0.210 g |

The active ingredient release of the tablets thus obtained was examined by the method specified in US Pharmacopoeia XXII (page 226). 80% by mass of the active ingredient were released within 5 minutes.

What we claim is:

1. A process for the preparation of tablets or film-coated tablets with increased active ingredient release, where said tablets comprise as active ingredient L-3,4-dihydroxyphenylalanine and L-alpha-hydrazino-alpha-methyl-3,4-dihydroxyphenyl propionic acid in a (3-12):1 mass to mass ratio, said process comprising
   (a) admixing any of L-3,4-dihydroxyphenylalanine and L-alpha-hydrazino-alpha-methyl-3,4-dihydroxyphenyl propionic acid, or both of them, with a hydrophilic diluent, and optionally with a colouring agent, wherein said diluent is lactose, or microcrystalline cellulose, or lactose and microcrystalline cellulose.
   (b) blending the mixture thus obtained with auxiliary agents conventionally used for the preparation of tablets and optionally with the other active ingredient, furthermore with a solution of stearin in an appropriate organic solvent, wherein said stearin is used in an amount of at least 1.5% related to the mass of the tablet,
   (c) drying and granulating the mixture thus obtained,
   (d) optionally admixing further auxiliary agent(s) to the dry granulate,
   (e) compressing it into tablets comprising 50 to 70% by mass of active ingredient and, if desired,
   (f) applying a film-coating onto the surface of the tablet thus obtained.

2. The process as claimed in claim 1, comprising using an alkanol comprising 2 to 4 carbon atoms as organic solvent.

3. The process according to claim 1, wherein said stearin is used in an amount of 1.5% to 2.5% related to the mass of the tablet.

4. The process according to claim 1, wherein said diluent is lactose and microcrystalline cellulose.

5. The process according to claim 2, wherein said solvent is ethanol or isopropanol.

6. The process according to claim 1, wherein said solution of stearin contains a binder.

7. The process according to claim 6, wherein said binder is methylmethacrylic acid ester polymer.

* * * * *